United States Patent

Rudnick et al.

[11] Patent Number: 5,552,071
[45] Date of Patent: *Sep. 3, 1996

[54] ALKYLATED DIPHENYL ETHER LUBRICANTS

[75] Inventors: Leslie R. Rudnick, Lawrenceville; Ross A. Kremer, Ringoes, both of N.J.; Derek A. Law, Yardley, Pa.

[73] Assignee: Mobil Oil Corporation, Fairfax, Va.

[*] Notice: The term of this patent shall not extend beyond the expiration date of Pat. No. 5,171,915.

[21] Appl. No.: 311,829

[22] Filed: Sep. 23, 1994

Related U.S. Application Data

[63] Continuation of Ser. No. 206,233, Mar. 3, 1994, abandoned, which is a continuation of Ser. No. 888,666, May 27, 1992, abandoned, which is a continuation-in-part of Ser. No. 637,425, Jan. 4, 1991, abandoned.

[51] Int. Cl.$^6$ .................. C10M 105/16; C10M 129/14; C10M 129/91
[52] U.S. Cl. .................. 508/581; 568/628; 568/635
[58] Field of Search .................. 252/52 R; 568/628, 568/635

[56] References Cited

U.S. PATENT DOCUMENTS

| | | | |
|---|---|---|---|
| 4,395,372 | 7/1983 | Kluttz et al. | 260/465 R |
| 4,664,829 | 5/1987 | Arakawa et al. | 252/52 R |
| 4,891,448 | 1/1990 | Garces et al. | 568/628 |
| 5,171,915 | 12/1992 | Forbus et al. | 585/462 |
| 5,254,274 | 10/1993 | Ho et al. | 252/52 R |

FOREIGN PATENT DOCUMENTS

| | | |
|---|---|---|
| 5144263 | 11/1976 | Japan . |
| 5573791 | 6/1980 | Japan . |

OTHER PUBLICATIONS

Campen et al., "Growing Use of Synlubes", Hydrocarbon Processing, Feb. 1982, pp. 75–80.

D. Klamen, "Lubricants and Related Products", Verlag Chemie, 1984, pp. 116–121.

*Primary Examiner*—Jerry D. Johnson
*Attorney, Agent, or Firm*—Ronald A. Bleeker; Malcolm D. Keen

[57] ABSTRACT

Monoalkylated diphenyl oxides are high-temperature stable lubricant fluids having excellent low temperature viscometrics, and excellent additive solubility. These monoalkylated products are obtained by the alkylation of diphenyl oxide using, for example, an olefin alkylating agent, usually in the $C_8$ to $C_{18}$ range, in the presence of an acidic zeolite alkylation catalyst such as USY, which provides the selectivity for the monoalkylated product.

6 Claims, No Drawings

ALKYLATED DIPHENYL ETHER LUBRICANTS

CROSS-REFERENCE TO RELATED APPLICATIONS

This application is a continuation of Ser. No. 08/206,233, filed Mar. 3, 1994, now abandoned, which is a continuation of Ser. No. 07/888,666, filed May 27, 1992, now abandoned, which is a continuation-in-part of Ser. No. 07/637,425, filed Jan. 4, 1991, now abandoned.

BACKGROUND OF THE INVENTION

1. Field of the Invention

This invention is directed to improved lubricant compositions comprising hydrocarbyl diphenyl ethers alone or in combination with synthetic or mineral oil fluids, and to mineral or synthetic lubricant compositions containing said ethers as additives therefor.

2. Description of Related Art

Polyphenyl ethers are known and have been used as lubricants in special applications. Polyphenyl ethers suffer from very high cost due to difficult synthesis and poor low temperature viscometrics.

Polyphenyl ethers are known for their high temperature properties as noted in D. Klamen's "Lubricants and Related Products", Verlag Chemie, 1984, pp. 116–121, and references contained therein, and also in, for example, the product bulletin for the commercial polyphenyl ether, OS-124 by Monsanto.

Many alkylation processes are known in the art and the alkylation methods of much of the prior art are primarily directed to polysubstituted or polyalkylated products. See, for example, JA 5557391 to Matsumura which discloses the dialkylation of diphenyl ethers over aluminum chloride. U.S. Pat. No. 4,395,372 to Klutz discloses the alkylation of benzene over a zeolite to obtain a predominantly polyalkylated product unless the alkylation takes place in the presence of sulfur dioxide. On the other hand U.S. Pat. No. 4,664,829 to Arakawa alkylates a mixture of materials to obtain both mono- and polysubstituted material. Arakawa uses Friedel-Crafts type catalysts. Garces, U.S. Pat. No. 4,891,448 discloses the alkylation of polycyclic aromatics over natural zeolites such as mordenite, offretite and gmelinite.

The present invention is directed to the alkylation of diphenyl ethers over zeolite catalysts which surprisingly results in a product which is predominantly or almost completely monoalkylated. Synthesized catalysts are preferred. Monoalkylated product comprises up to at least about 99% of the alkylation process in accordance with the present invention. In some instances the monoalkylation rate is 100%.

Incorporation of linear alkyl hydrocarbon groups into diphenyl ether eliminates the above-referenced problems and provides a novel, relatively inexpensive lubricant having excellent low temperature viscometrics. The use of these adducts as a lubricant or lubricant additive in either mineral or synthetic lubricants is unique and provides improved properties and performance benefits due to an inherent synergism.

BRIEF SUMMARY OF THE INVENTION

The hydrocarbon compositions of the present invention relate to improved thermally and oxidatively stable fluids. These may be used optionally as liquid lubricants or in liquid lubricant compositions, and as solid lubricants or in solid lubricant compositions including greases, such as polyurea, lithium carboxylate or clay-thickened greases.

These hydrocarbon compositions may also be used in combination with additives, for example, antioxidants, EP/antiwear agents, inhibitors, detergents and dispersants, and viscosity index improvers. Non-limiting examples of antioxidants include phenols which can be hindered and aromatic amines. Non-limiting examples of EP/antiwear additives include zinc phosphorodithioates, sulfurized esters, sulfurized olefins, phosphonates, phosphites, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

The hydrocarbon compositions of this invention can be used alone or in combination with other synthetic and/or mineral oil fluids.

The products obtained from the reaction of a linear olefin and diphenyl ether in the presence of zeolite catalysts are unique not only in composition and structure but in utility. Part of the uniqueness is derived from the specific reaction over zeolite catalysts; generally, they have a higher VI at a given viscosity. The incorporation of various alkyl groups into the diphenyl ether structure provides compositions of different viscosity and low-temperature properties. More particularly, the diphenyl ether (DPE) lubricant fluid comprising a substantially monoalkylated diphenyl oxide (DPO) or diphenyl ether (DPE) produced by alkylating a DPE with an alkylating agent in the presence of an acidic zeolite catalyst. The alkyl substituent on the ADPO (alkylated diphenyl oxide), which may optionally contain S, N, O, P or F substituents, is usually in the $C_3$ to $C_{500}$ carbon number range.

It is therefore an object of this invention to provide novel lubricant compositions wherein the hydrocarbyl diphenyl ethers in accordance with the invention comprise all or a major proportion of the lubricant fluid and also to provide novel lubricant compositions containing minor proportions of said diphenyl ethers as additives or in blends with other lubricant fluids such as synthetic polyalphaolefins.

BRIEF DESCRIPTION OF THE DRAWINGS

FIGS. 1 and 2 are GC (Gas chromatography) MS (mass spectrometry) graphs of product in accordance with the invention.

DESCRIPTION OF THE PREFERRED EMBODIMENTS

The novel class of products of the present invention can be characterized as hydrocarbyl adducts of diphenyl ethers or diphenyl oxides (DPO). The hydrocarbyl alkylating agent can be selected from the group consisting of alkyl, alkenyl, alkynyl, arylalkyl, alkylaryl or is cyclic and/or linear or branched. The hydrocarbyl group can optionally contain S, N, O, P and/or F substituents or substituent groups or mixtures thereof. The hydrcarbyl group of the alkylating agent can contain from 3 to about 500 carbon atoms and preferably from about 6 to about 50 carbon atoms and most preferably from about 8 to about 18 carbon atoms. The preferred alkyating agents are olefins, especially 1-olefins. The products are substantially or completely monoalkylated. The percentage of monoalkylation varies from about 98% to 100%.

One preferred method of reaction between the alkylating agent and the diphenylether is the combination of these reactants in the presence of zeolite catalysts. The zeolite catalysts should be at least partly in the acidic (H) form to confer the acidity for the reaction but may contain other cations also such as ammonium ($NH_4+$). The zeolite is preferably a large pore zeolite such as the faujasites, e.g., zeolites X, Y, USY, UHP-Y, ZSM-20 or zeolite beta. Another zeolite which may be used is zeolite MCM-22. Zeolite USY is sold commercially as Octacat cracking catalyst. This reaction is affected at temperatures ranging from ambient to 350° C., preferably from 100°–250° C. and most preferably from 180°–240° C. over the period required to produce conversion of reactants to desired product. Optionally, the reaction can be performed in a batch or semi-batch mode by continuous or partial addition of catalyst or hydrocarbyl substituent to the diphenyl ether. Catalyst can be used at levels ranging from 1 gram/mole of aromatic to 100 grams/mole of aromatic, preferably from 5 g/mole of aromatic to 50 grams/mole of aromatic, and most preferably from 10–30 grams catalyst/mole of aromatic. The catalyst may be steamed, calcined or fresh.

The above preferred method demonstrates the use of the catalysts of choice. MCM-22 is disclosed in U.S. Pat. No. 4,954,325 which is incorporatd herein in its entirety by reference. It is also described in U.S. Pat. No. 5,100,534, which is incorporated herein in its entirety by reference, as a crystalline aluminosilicate zeolite. MCM-22 is also described in U.S. Pat. No. 5,103,066 as having a CI (constraint index) of 1.5 at 454 C. U.S. Pat. No. 5,103,066 is incorporated herein by reference.

Constraint Index (CI) values for some typical zeolites are given below.

| | CI (at test temperature) |
|---|---|
| ZSM-5 | 6–8.3 (371° C.–316° C.) |
| ZSM-22 | 7.3 (427° C.) |
| MCM-22 | 1.5 (454° C.) |
| Dealuminized Y | 0.5 (510° C.) |

The method by which Constraint Index of acidic zeolites is determined is described fully in U.S. Pat. No. 4,016,218 incorporated herein by reference for details of the method. The above-described CI is a highly important definition of the zeolites which are useful in the process of the present invention.

The alpha value is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 $sec^{-1}$). The alpha test is described in U.S. Pat. No. 3,354,078 and in *J. Catalysis*, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in *J. Catalysis*, 61, 395 (1980).

FCC (fluid catalytic cracking) catalysts based on ultrastable Y type (USY) zeolites are well known in the art to make gasoline having a higher octane number than FCC catalysts based on rare earth exchanged Y (REY) or calcined rare earth exchanged Y (CREY); see U.S. Pat. No. 5,102,530 which is incorporated herein by reference. It is further disclosed in U.S. publication/notice H 449 (Mar. 1, 1988) to Rudesill that the commercially available FCC cracking catalyst (Octacat) comprises about 40% Ultrastable Type Y zeolite combined with a silica-alumina sol binder and kaolin matrix and that preferably the USY containing Octacat may comprise from about 15 to about 60 wt. % USY and more preferably from about 35 to about 45 wt. % USY. H 449, filed Jul. 3, 1987 and published Mar. 1, 1988 to Rudesill is incorporated herein by reference.

The monoalkylated products obtained with the zeolite catalysts exhibit superior properties in comparison to the alkylated DPO prepared by reaction of the alkylating agent with the diphenyl ether in the presence of $AlCl_3$ and other proton, and Lewis acids as described in G. A. Olah's "Friedel-Crafts and Related Reactions", Vol, I, 1963, Interscience Publishers.

As noted hereinabove the novel products in accordance with the invention are substantially, i.e., up to 100% and at least about 98% monoalkylated. FIGS. 1 and 2 which are GCMS graphs of alkylated $C_{14}$ diphenyl ether (oxide) products in accordance with the invention corroborate this. Further evidence of this extrordinary high degree of monoalkylation is contained in Table 4 below which compares the alkylation of DPO with $C_{14}$, $C_{16}$ and $C_{18}$ olefins using Octacat Y zeolite catalyst with that of $C_{10}$ and $C_{14}$ DPO produced using a BF3 catalyst. There are only trace amounts of dialkylated material present as clearly shown in the Figures while said Table discloses by GCMS analysis of the product that it is 100% monoalkylated. This Table also discloses the superiority of zeolite catalysts over a non-zeolite catalyst such as BF3 in achieving exclusively monoalkylation. The USY catalyst produced 100% monoalkylation while the BF3 only obtained 56% monoalkylation as well as 44% polyalkylation.

When it is desired that the fluid compositions of the present invention are to be used alone or in combination with other synthetic and/or mineral oil fluids, the below described oils of lubricating viscosity may be used.

When the ADPO is used as the base fluid or feedstock it will generally have a viscosity range varying from about 3 to about 20 cSt at 100° C. with a preferred range of 3.5 to 10.

The fluids in accordance with the invention have been found to be highly useful when combined or blended with synthetic or mineral based fluids and particularly with ester-containing fluids such as synthetic polyalphaolefins (PAO). Any suitable blending ratio may be used, for example, a blend of 20% ADPO and 80% PAO has been found to be very advantageous. However, the ADPO may constitute a majority of the blends up to about 80–100% or less than 100%. It is noted that ADPO fluids may be used as replacements for or as components of current commercial lubricant formulations.

In general, mineral oils, both paraffinic, naphthenic and mixtures thereof, employed as the lubricant, or grease vehicle, may be of any suitable lubricating viscosity range, as for example, from about 1.0 cSt at 100° C. to about 1000 cSt at 100° C. and preferably, from about 2.0 to about 60 cSt at 100° C. The preferred oils may have viscosity indexes ranging to about 150. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polypropylene glycol, polyethylene glycol, trimethylpropane esters, neopentyl and pentaerythritol esters, di(2-ethylhexyl) sebacate, di(2-ethylhexyl) adipate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers.

When used as additives the materials in accordance with the invention have the ability to improve the antiwear characteristics and friction reducing characteristics of various oleaginous materials such as hydrocarbyl lubricating media which may comprise liquid oils in the form of either a mineral oil or a synthetic oil, or in the form of a grease in which the aforementioned oils are employed as a vehicle.

It is to be understood, however, as mentioned hereinabove that the compositions contemplated herein can also contain other materials. For example, corrosion inhibitors, extreme pressure agents and the like can be used as exemplified respectively by metallic phenates sulfonates, polymeric succinimides, non-metallic or metallic phosphorodithioates and the like. These materials do not detract from the value of the compositions of this invention, rather the materials enhance the beneficial characteristics of the disclosed diphenyl ethers.

The following examples are exemplary only and are not intended to limit the invention.

EXAMPLE 1

To a vigorously stirred mixture of diphenyl ether (170 g, 1.0 mole) and 1-tetradecene (196 g, 1.0 mole) in a flask fitted with thermocouple and reflux condenser was added 15 g of FCC Octacat USY catalyst. The mixture was heated to 200° C. with stirring for six hours. After cooling to room temperature, the mixture was filtered to remove catalyst and vacuum distilled to 170° C. at 0.5–1.5 mmHg to remove unreacted starting materials.

EXAMPLE 2

Using the procedure in Example 1, diphenyl ether (170 g, 1.0 mole) and 1-tetradecene (196 g, 1.0 mole) were reacted using 30 grams of FCC Octacat USY catalyst.

EXAMPLE 3

Using the procedure in Example 1, diphenyl ether (120 g, 1.0 mole) and 1-dodecene (168.32 g, 1.1 moles) were reacted using 15 grams of FCC Octacat USY catalyst.

EXAMPLE 4

To a stirred mixture of 1-octene, 224.2 g (2 moles), and diphenyl ether, 170 g (1 mole), was added 2.0 grams of anhydrous $AlCl_3$, and heated at reflux for six hours. The mixture was cooled, washed to remove inorganic materials, dried over anhydrous $MgSO_4$. Gas chromatographic analysis showed essentially complete reaction of starting material. Color of this material $\geq 5$ whereas the product of Example 1 was $\leq 2.0$.

EXAMPLE 5

Using the procedure in Example 4, 1-decene 168 g (1 mole) and diphenyl ether (170 g, 1 mole) were reacted with $AlCl_3$ (2 grams) at reflux for six hours. Vacuum distillation of the washed organic mixture to 170° C. at 0.5–1.5 mmHg resulted in the desired hydrocarbyl diphenyl ether product.

Typical properties of exemplary hydrocarbyl diphenyl ethers are shown in Table 1.

TABLE 1

| Hydrocarbyl | $C_{14}$ | $C_{14}$ | $C_{14}$ |
| --- | --- | --- | --- |
| KV @ 100° C., cSt | 4.0 | 3.8 | 10.7 |
| VI | 111 | 94 | 103 |
| Pour Point (°C.) | $\leq -54$ | $\leq -54$ | $-40$ |
| Flash Point (°F.) | — | 435 | 475 |

Performance Evaluation as a Lubricant Having Improved Antiwear

Tetradecene alkylated diphenyl ether was compared to polyolefin base stock in a Four-Ball Wear test. The results show that at higher load, the alkyl diphenyl ether produced less wear than the other base stock, without any adverse effect on coefficient of friction (f).

The antiwear properties of the examples were evaluated using the Four Ball Wear Test as shown in the Table below. The results clearly exhibit the excellent antiwear properties inherent in these unique compositions.

In the Four Ball Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 5200 steel for thirty minutes under 40 kg load at 600 and 1800 rpm and 200° F. If additional information is desired consult test method ASTM D2266 and/or U.S. Pat. No. 4,761,482.

K, as reported in the Table, is the wear coefficient calculated from the wear volume, V, of the stationary ball. The wear volume is calculated from the wear scar diameter D in mm as follows:

$$V = [15,5\ D3 - 0.001033L]D \times 103\ mm3$$

where L is the machine load in kg. This equation considers the elastic deformation of the steel balls.

Wear Coefficient K

Dimensionless K is defined as $$K = \frac{VH}{dN}$$

where

V = wear volume, mm3

H = hardness 9725 kg/mm2 for 52100 steel d = (23.3 mm/rev) (RPH×Time)

N = (0.408) (Load in kg)

The Four-Ball Wear Test results demonstrate the excellent antiwear properties of these compositions when used in synthetic oils.

TABLE 2

Four-Ball Wear Test Results
(200° F./40 Kg/30 min)

|  | 600 RPM | | 1800 RPM | |
| --- | --- | --- | --- | --- |
|  | k | f | k | f |
| $C_{14}$-DPE | 13.2 | 0.11 | 431 | 0.11 |
| polyolefin basestock | 11.4 | 0.09 | 1300 | 0.09 |

Performance Evaluation as a Lubricant with Improved Additive Solubility

To a synthetic lubricant base stock was added 4.0 wt % of sulfurized isobutylene (as generally described by A. G. Horodysky in U.S. Pat. No. 3,703,504) and 0.5 wt % of a hindered phenolic inhibitor obtained from Ethyl Corp. as Ethyl 702. The mixture of additives was insoluble in the base stock and the sample was cloudy. To this mixture was added 21 wt % $C_{14}$ alkylated diphenyl ether. The sample was mixed; the additives completely dissolved and the mixture became clear.

Improved Thermal and Light Stability of Alkyl Diphenyl Ethers over Other Lubricant Classes

TABLE 3

A. Thermal Stability Test

| Sample | % Viscosity Change After 72 hrs at 288° C. |
| --- | --- |
| $C_{14}$-DPE (Sample 1) | −1.4 |
| $C_{14}$-DPE (Sample 2) | −3.0 |
| Commercial Synthetic Lubricant (Sample 1) | −14.8 |
| Commercial Synthetic Lubricant (Sample 2) | −19.4 |
| Commercial Synthetic Lubricant (Sample 3) | −38.8 |
| Commercial Synthetic Lubricant (Sample 4) | −60.9 |
| Commercial Synthetic Lubricant (Sample 5) | −67.9 |
| Lube Ester | −34.2 |

B. Oven Storage Tests (150° C./5 days)

| | Color (Before) | (After) |
| --- | --- | --- |
| $C_{14}$-DPE (Octacat USY) | 2 | 2.5 |
| $C_{14}$-DPE (AlCl$_3$) | 5.5 | — |
| Commercial Synthetic Lubricant (Sample 1) | 1 | −1.5 |
| 200-Second Solvent Paraffinic Neutral Lubricating Oil | 2 | ≧5.5 |

The results of thermal stability and storage stability tests are shown below:

Light stability was good as no color change or precipitate was observed over two months.

TABLE 4

COMPARISON OF OCTACAT Y AND BF3 ADPOs
ADPOs: Effect of Catalyst on ADPO Properties

| CATALYST: | Octacat Y | | | BF3 | |
| --- | --- | --- | --- | --- | --- |
| 1-OLEFIN: | C14 | C16 | C18 | C10 | C14 |
| KV100 | 3.8 | 4.4 | 5.1 | 6.0 | 5.8 |
| VI | 76 | 98 | 108 | 106 | 110 |
| Pour Point (C) | −54 | −40 | −35 | <−54 | −45 |
| DSC T(onset) | 200–205 | | | 191 | 205 |
| Thermal Stability % KV40 loss (310° C./40 hr.) | | 4 | | 13 | 11 |
| Hot Tube Rating: | | | | | |
| 300° C. | | 2 | | | 2+ |
| 310° C. | | 3 | | | 5+ |
| 315° C. | | 4 | | | 7 |
| B-10 | | 5–10 | | | 14 |
| % KV100 increase (260° F./40 hr.) | | | | | |
| GC Analysis | | | | | |
| monoalkyl | | 100 | | | 56 |
| dialkyl | | 0 | | | 34 |
| trialkyl | | 0 | | | 10 |

The use of alkylated diphenyl ether as a suitable replacement for components of current lubricant formulations is highly desirable. For example, synthetic and/or mineral based lubricant composition containing esters for improved additive solubility would be significantly improved by replacement with alkylated diphenyl ether due to its excellent thermal stability and excellent additive solubility. Alkyl diphenyl ether prepared as described herein provide excellent base stock properties and could themselves serve as the base stock in formulations for various applications, for example, applications where high temperatures are maintained.

What is claimed:

1. A process for the preparation of a high-temperature stable lubricant fluid or lubricant additive comprising reacting in the presence of a zeolite catalyst (1) an olefinic alkylating agent containing from 12 to about 500 carbons and optionally containing S, N, O, P, F, or mixtures thereof, and (2) a diphenyl ether wherein the reaction temperature varies from ambient to about 350° C., the molar ratio of said alkylating agent to diphenyl ether varies from 0.5:1.0 to about 10.0:1.0, the amount of catalyst varies from 5 to about 100 grams of catalyst to about 1 mole of diphenyl ether, and the reaction product comprising a substantially monosubstituted adduct.

2. The process of claim 1 wherein the alkylating agent is a $C_8$ to $C_{18}$ alpha-olefin.

3. The process of claim 1 wherein the catalyst is selected from zeolites X, Y, UHP-Y, ZSM-20, zeolite beta and MCM-22.

4. The process of claim 1 wherein the catalyst is an ultrastable Y zeolite catalyst.

5. The process of claim 1 wherein the alkylating agent is 1-tetradecene and the catalyst is an ultrastable Y zeolite catalyst.

6. The process of claim 1 wherein the alkylating agent is 1-dodecene and the catalyst is an ultrastable Y zeolite catalyst.

* * * * *